United States Patent [19]
Tran

[11] Patent Number: 5,410,313
[45] Date of Patent: * Apr. 25, 1995

[54] FUNCTIONAL RADAR WARNING RECEIVER BACK-UP GENERATOR

[75] Inventor: My Tran, Albuquerque, N. Mex.

[73] Assignee: Honeywell Inc., Minneapolis, Minn.

[*] Notice: The portion of the term of this patent subsequent to Feb. 15, 2011 has been disclaimed.

[21] Appl. No.: 977,322

[22] Filed: Nov. 17, 1992

[51] Int. Cl.⁶ .............................................. G01S 7/42
[52] U.S. Cl. .................................... 342/13; 342/192
[58] Field of Search ............... 342/13, 14, 20, 192, 342/184, 195; 364/423, 517

[56] References Cited

U.S. PATENT DOCUMENTS

| | | | |
|---|---|---|---|
| 4,694,298 | 9/1987 | Milan | 342/89 |
| 4,876,545 | 10/1989 | Carlson et al. | 342/14 |
| 4,916,450 | 4/1990 | Davis | 342/71 |
| 5,029,169 | 7/1991 | Smyk | 371/19 |
| 5,053,722 | 10/1991 | Kuo et al. | 331/2 |
| 5,287,110 | 2/1994 | Tran | 342/13 |

Primary Examiner—Gilberto Barrón, Jr.
Attorney, Agent, or Firm—Ronald E. Champion; Craig J. Lervick

[57] ABSTRACT

A functional radar warning receiver backup generator. A functional radar warning receiver backup generator provides threat information in the total absence or partial absence of the radar warning receiver information. Radar warning receiver information such as radar detection data and radar identification data is also generated by other systems such as the Pulsed Radar Jammer and the Continuous Wave Radar Jammer. An on-board computer processes and presents the back-up information to the pilot as if the Radar Warning Receiver was still operational. Voice and video functions of the Radar Warning Receiver are also displayed and presented to the pilot. Partial back-up and full back-up of the Radar Warning Receiver are provided. A temporal data correlation algorithm, a radar emitter ID conversion algorithm, cross sensor correlation algorithm and prioritization algorithm provide the back-up data.

17 Claims, 9 Drawing Sheets

FUNCTIONAL RADAR WARNING RECEIVER BACK-UP GENERATOR

UNITED STATES GOVERNMENT RIGHTS

The United States Government has acquired certain rights in this invention through government Contract No. DAA B07-87-C-H041 awarded by the Department of the Army.

BACKGROUND OF THE INVENTION

1. Field of the Invention

This invention relates to an aircraft survivability equipment apparatus and more particularly to a functional radar warning receiver back-up generator for an aircraft survivability equipment system.

2. Discussion of the Prior Art

In the prior art, individual aircraft survivability equipment (ASE) sensors are used as stand-alone systems. The use of such systems in a stand-alone manner results in high pilot workloads. Further, in such systems only a limited amount of threat data is presented to the pilot. Data provided by various ASE subsystems such as pulsed radar jammers, CW radar Jammers and missile approach detectors have previously not been used to provide a comprehensive and coherent picture of the threat environment. Thus prior art systems often do not present adequate data in a readily understood format to enable the pilot to quickly and completely assess a given threat environment.

Prior art aircraft survivability systems do not provide a Radar Warning Receiver (RWR) back-up capability. This capability would enhance the probability of mission completion. When the RWR indicates that the system is either inoperative, or that a partial receiving capability has been lost due to a detected failure, the flight crew has to make a quick decision as to whether a mission should be completed with a reduced or degraded radar warning capability or whether a mission should be terminated, for example.

It is therefore the motive of the invention to provide capabilities to increase aircraft survivability and to increase the likelihood of mission completion by providing a functional radar warning receiver back-up generator.

SUMMARY OF THE INVENTION

The invention provides a functional radar warning receiver back-up generator that provides threat information in the total absence or partial absence of radar warning receiver information. Radar warning receiver information such as radar detection data and radar identification data is generated by systems such as the pulsed radar jammer and the continuous wave radar jammer. The information from these systems is processed and presented to the pilot as if the radar warning receiver was operational. The invention provides an automatic back-up for both the voice and video functions of the radar warning receiver if the radar warning receiver loses some of the threat coverage capability indicated by the system status of the receiver. The invention provides two modes of operation, the first mode is partial radar warning receiver back-up and the second mode is full radar warning receiver back-up. The invention uses a temporal data correlation apparatus and a radar emitter ID conversion apparatus to provide data to the back-up functions.

It is an object of the invention to provide a functional radar warning receiver back-up generator.

It is yet another object of the invention to provide a functional radar warning receiver back-up generator that increases the probability of mission completion by providing functional radar warning receiver information in the absence of the radar warning receiver.

It is yet a further object of the invention to provide a functional radar warning receiver back-up generator that provides increased mission reliability by generating threat data based on the remaining warning systems.

Other objects, features and advantages of the present invention will become apparent to those skilled in the art through the description of the preferred embodiment, claims and drawings herein where like numerals refer to like elements.

DETAILED DESCRIPTION OF THE PREFERRED EMBODIMENT

Figure 1:
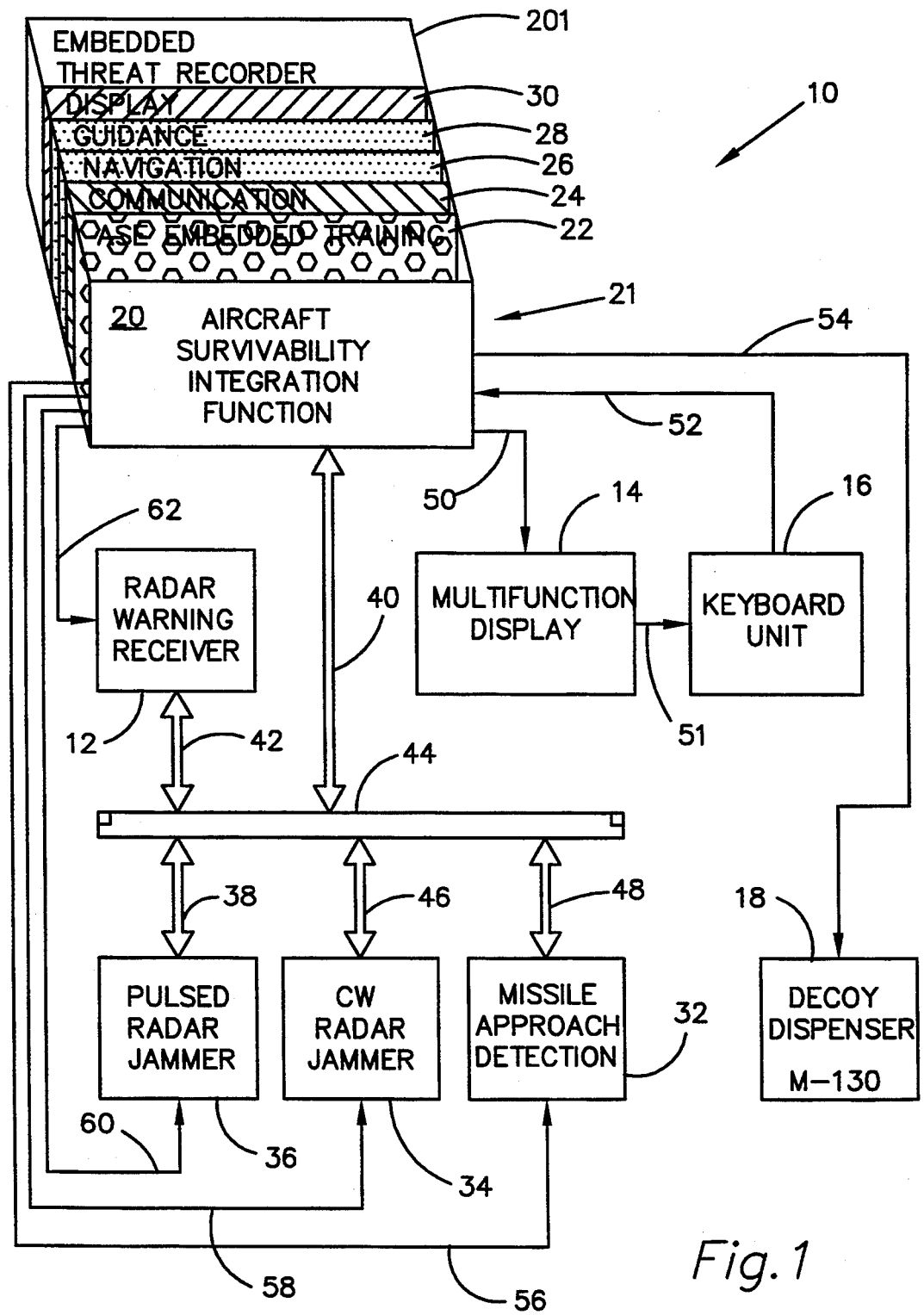
FIG. 1 shows a high level system diagram of one embodiment of the aircraft survivability integration equipment system as employed by the invention.

Now referring to FIG. 1, a high level system diagram of one embodiment of the aircraft survivability integration equipment system 10 as employed by the invention is shown. Aircraft survivability system 10 includes aircraft survivability integration functions 21, a multifunction display 14, a keyboard unit 16, a continuous wave (CW) radar jammer 34, a missile approach detector 32, a pulsed radar jammer 36, a radar warning receiver 12 and a decoy dispenser 18. The aircraft survivability integration functions 21 further include an aircraft survivability integration function 20, an aircraft survivability equipment embedded training apparatus 22, communication apparatus 24, navigation apparatus 26, guidance apparatus 28, display apparatus 30 and an embedded threat data recorder 201. The radar warning receiver 12, pulsed radar jammer 36, CW radar jammer 34, missile approach detector 32, multifunctional display 14, keyboard unit 16 and decoy dispenser 18 are standard units. The radar warning receiver 12, pulsed radar jammer 36, CW radar jammer 34 and missile approach detector 32 all communicate with each other and the aircraft survivability integration functions 21 through a data bus 44. The data bus 44 may advantageously be a MIL standard 1553 data bus or equivalent. In one example of the invention, the radar warning receiver (RWR) 12 communicates with the data bus through communication lines 42, the pulsed radar jammer 36 communicates with the data bus through communication lines 38, the CW radar jammer 34 communicates to the data bus by communication lines 46 and the missile approach detector 32 communicates to the data bus by communication lines 48. In this way, the sensors in the system which comprise the radar warning receiver 12, pulsed radar jammer 36, CW radar jammer 34 and missile approach detector 32 can receive and transmit data to the aircraft survivability integration functions 21. In addition, the aircraft survivability integration functions 21 may be hardwired to the plurality of sensors. This introduction of hardwired lines to the individual sensors provides a redundancy feature in the system which guards against failure of the data bus 44. For example, the radar warning receiver may be wired by lines 62 into the aircraft survivability integration function 20, the pulsed radar jammer by lines 60, the CW radar jammer by lines 58 and the missile approach detector by lines 56. Hard wire and bus interfaces are typically provided with such ASE devices as are conventionally available.

The multifunction display 14 is controlled by the display apparatus 30 and is wired to the display apparatus 30 in aircraft survivability integration function 20 by lines 50. The multifunction display also interfaces with the keyboard unit 16, which may be a standard keyboard unit, by lines 51. The keyboard unit 16 is also wired into the communication apparatus 24 by lines 52. Control lines 54 are connected from the ASE integration functions 21 to the decoy dispenser 18.

Figure 2:
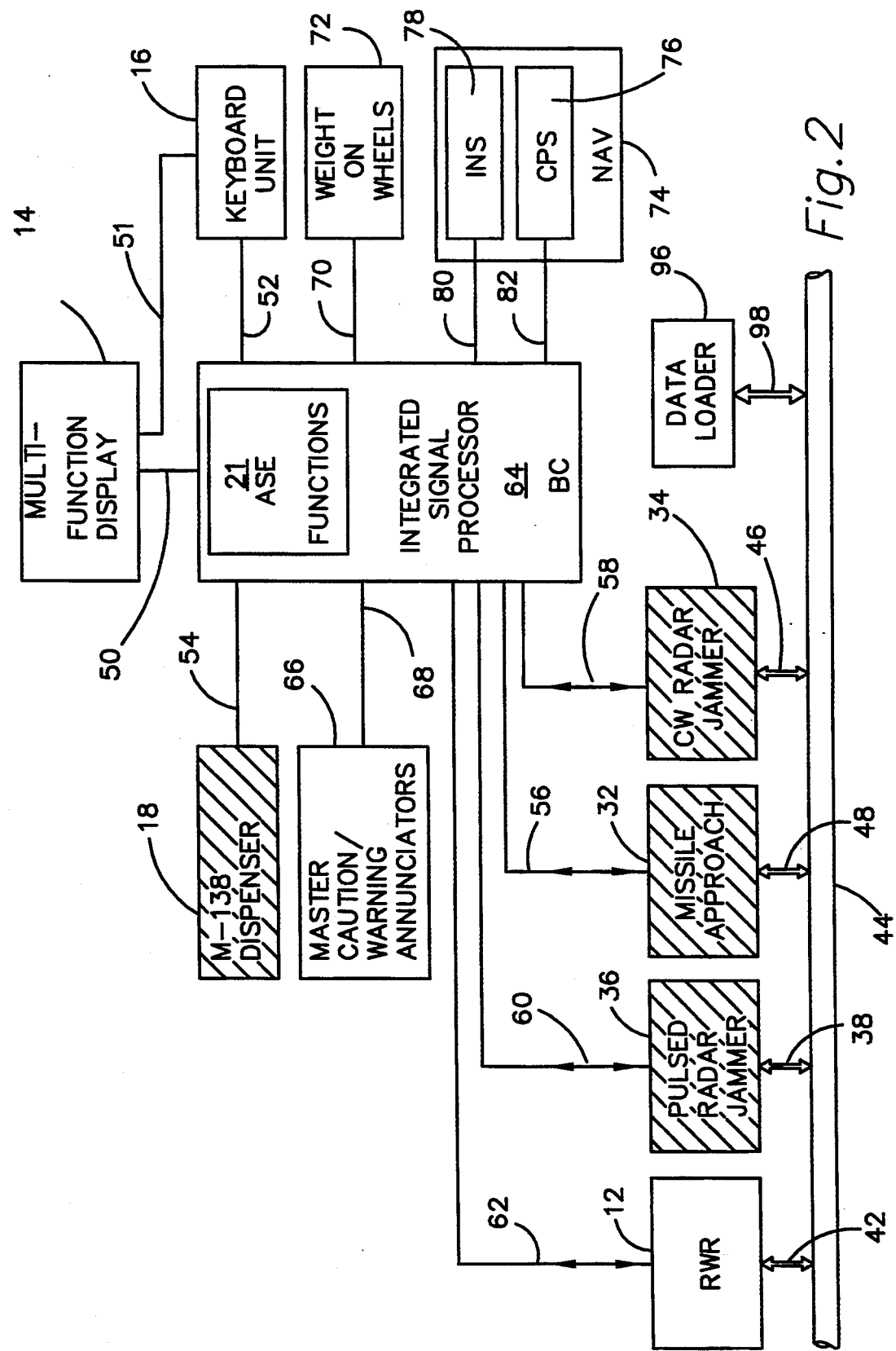
FIG. 2 shows a more detailed block diagram of the aircraft survivability equipment integration system 10 which is integrated into an aircraft survivability equipment/avionics control system (ASE/ACS).

Now referring to FIG. 2, a more detailed block diagram of the aircraft survivability equipment integration system is shown as integrated into an aircraft survivability equipment/avionics control system (ASE/ACS). The aircraft survivability equipment/avionics control system is used to integrate control and display of an ASE suite of devices such as the radar warning detector and jammers as well as selected military communication and navigation systems. Those skilled in the art will understand that the configuration shown in the block diagram of FIG. 2 is one example and does not so limit the invention. In the system shown in FIG. 2, the aircraft survivability integration functions 21 is embedded in an integrated signal processor 64. The integrated signal processor 64 may advantageously comprise a microprocessor, digital signal processor or an equivalent device. Also connected to the integrated signal processor 64 is a master caution/warning annunciator 66 which is connected to the integrated signal processor 64 by line 68, a weight on wheels sensor 72 which is connected by line 70, and navigation systems 74 which are connected by lines 80 and 82. The navigation equipment advantageously includes an inertial navigation system (INS) 78 and a global positioning system (GPS) 76. A data loader 96 is connected via lines 98 to bus 44. The data loader 96 is a conventional data loader and may be used to input flight information and other parameters into the signal processor 64 prior to an aircraft embarking on a particular flight plan. The other components are as shown in FIG. 1 and operate similarly. Those skilled in the art will recognize that the ASE equipment including the radar warning sensor, jammers and missile approach detector are well known standard units.

The weight on wheels sensor 72 is a known sensor which communicates with the signal processor 64 and provides an enable signal 70 which enables certain built-in test functions to be performed when the aircraft is on the ground. These built-in test functions may be a part of the radar warning receiver 12, the pulsed radar jammer 36, the missile approach detector 32 and the continuous wave radar jammer 34.

The integrated signal processor 64 also serves as a bus controller using well known control signals. The four ASE subsystems, RWR 12, pulsed radar jammer 36, missile approach detector 32 and CW radar jammer 34 may be advantageously configured as remote terminals.

The ASE/ACS system provides a fail active state with regard to the ASE suite. If, for example, the integrated signal processor 64 should fail, or power is removed from the unit, the ASE subsystems may assume their most active states. The ability to fire flares and chaff is not impaired by a data bus failure in this redundant configuration. In order to insure this, flare and chaff fire switches are wired directly into the decoy dispenser 18 and are not controlled by the ASE/ACS in the event of a data bus failure. In the alternative, the decoy dispenser 18 may be fired automatically through the aircraft survivability integration functions 21 when an appropriate signal is received from any one or more of the subsystem sensors, such as the radar warning receiver.

Figure 3:
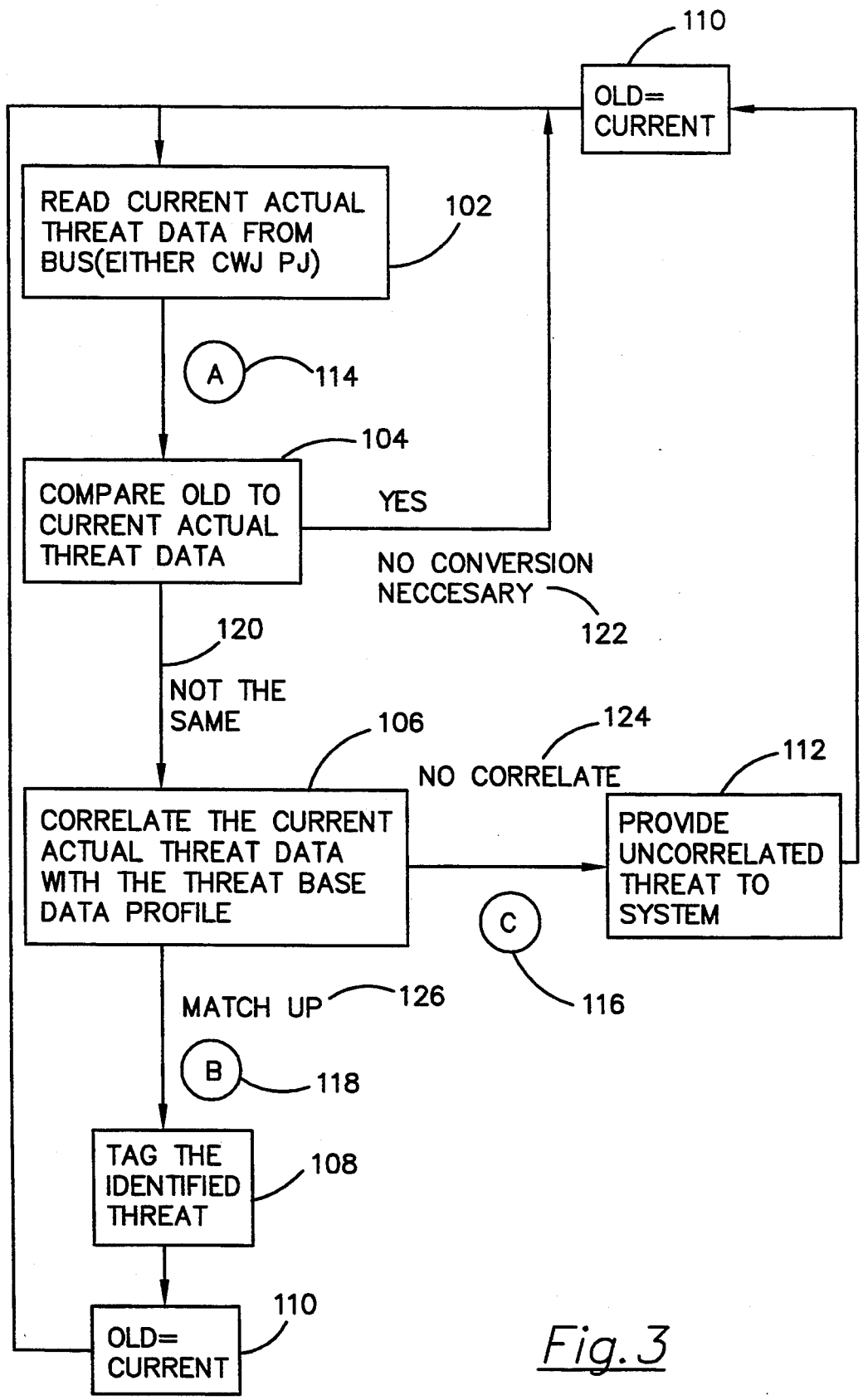
FIG. 3 shows a method of the invention that is used to convert the current actual threat data, that is sent to the system bus from either the continuous wave radar jammer or the pulsed radar jammer, to either an un-correlated threat or an identified threat.

Now referring to FIG. 3 which shows the method of the invention used to convert current actual threat data from the system data bus from either the continuous wave radar jammer or the pulsed radar jammer to either an un-correlated threat or an identified threat. The threat data base is composed of a number of sub-elements and parameters. A threat data base may be input into the system and stored in memory by any well-known means. The threat data base advantageously contains threat parameters including threat types which include, in one preferred embodiment of the invention, a missile, antiaircraft gunfire, a fighter, or other threats identified by the aircraft. Each threat type has an associated set of parameters which, in one preferred embodiment of the invention, include frequency of the threat signal, amplitude of the threat signal, pulse repetition frequency, pulse repetition interval, angle of arrival, and operational mode of the threat. Those skilled in the art will recognize that other parameters may be used in the method of the invention. Those skilled in the art will recognize that either all the parameters may be included in the threat data base or just a few. The threat data base comprises a profile of known threats that may be encountered by the aircraft.

FIG. 3 shows the processing of data from a current actual threat as read from the jammer radars. The threat data is provided on the data bus 44 as shown in FIGS. 1 and 2. The process of the invention starts at step 102 wherein the current actual threat data from the data bus is read. This data is also available directly to the system processor 64 from the hardwire connections 58, 60 and from the radar jammers 34, 36. Those skilled in the art will recognize that the bus method of communication provides more robust threats. The process flows to step 104 where previously received old threat data is compared to just received current actual threat data. Step 104 compares on a logical basis the old detected threat and the current detected threat. The comparison of different threat data occurs in different time slices. The old threat data occurred at the last sample period as indicated in step 110. The comparison of the various threat data parameters can occur either through known accepted methods such as boolean comparisons or threshold comparisons which compare an upper bound to a lower bound of the parameters, or a comparison of whether or not the parameters are within a window of parameter values. Alternate methods of comparison understood by those skilled in the art may be used such as fuzzy logic-based comparisons. The process flows to step 106 if the system is in a state that indicates the old and the current actual threat data is not the same. At step 106 the process correlates the current actual threat data with threat profiles from the threat data base. In one preferred embodiment of the invention, the current actual threat is compared against each element of the threat data base using the comparison methods used in step 104. If the threats correlate and match up as indicated by state 126, the process flows to step 108 where the identified threat is tagged. The process then flows to step 110 to set the old actual threat data to equal the current actual threat data. The process then proceeds to step 114.

Figure 5:
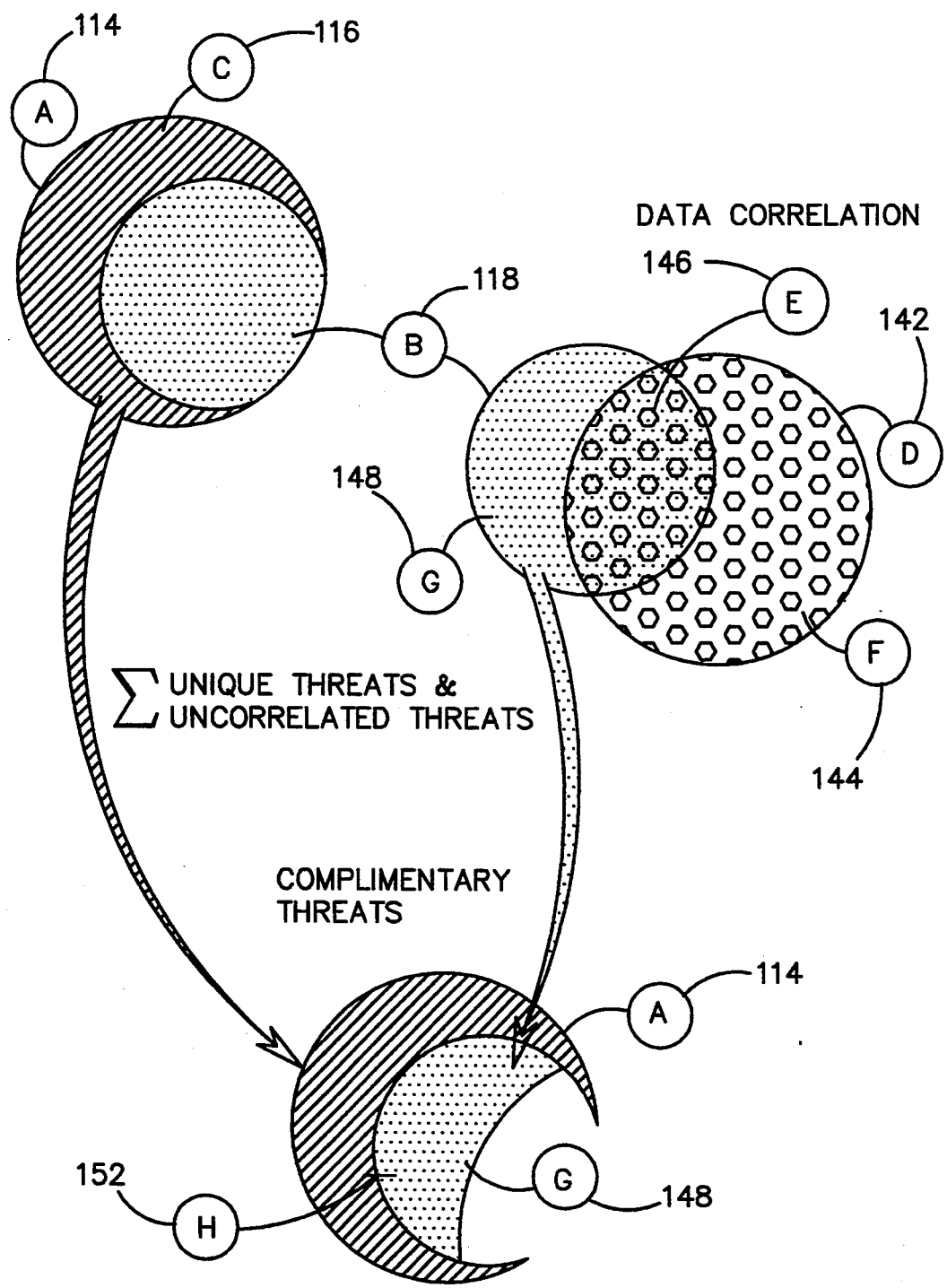
FIG. 5 shows a data flow diagram showing the various data sets of the invention in a Venn diagram fashion.

The processor creates different sets of data which are correlated as shown in FIG. 5 which is described in detail below. At step 102, the process takes data from one of the radar jammers which is designated as data set A 114. In step 106, a data set labeled C 116 is generated which represents an un-correlated current actual jammer threat data. This data is presented to process step 112 to provide un-correlated threat data to any system using the method of the invention. The process then flows to step 110 which sets the old threat data to the current threat data. Next, the process returns to step 102. The process step 106 generates a data set called B 118 which is the matched-up correlated current actual jammer threat data. If in process 104 the comparison to check old threat data against current threat data results in the old and the current being the same, then the process flows to step 102 to read the next current actual threat data from the bus or from the hardwired system.

Figure 4:
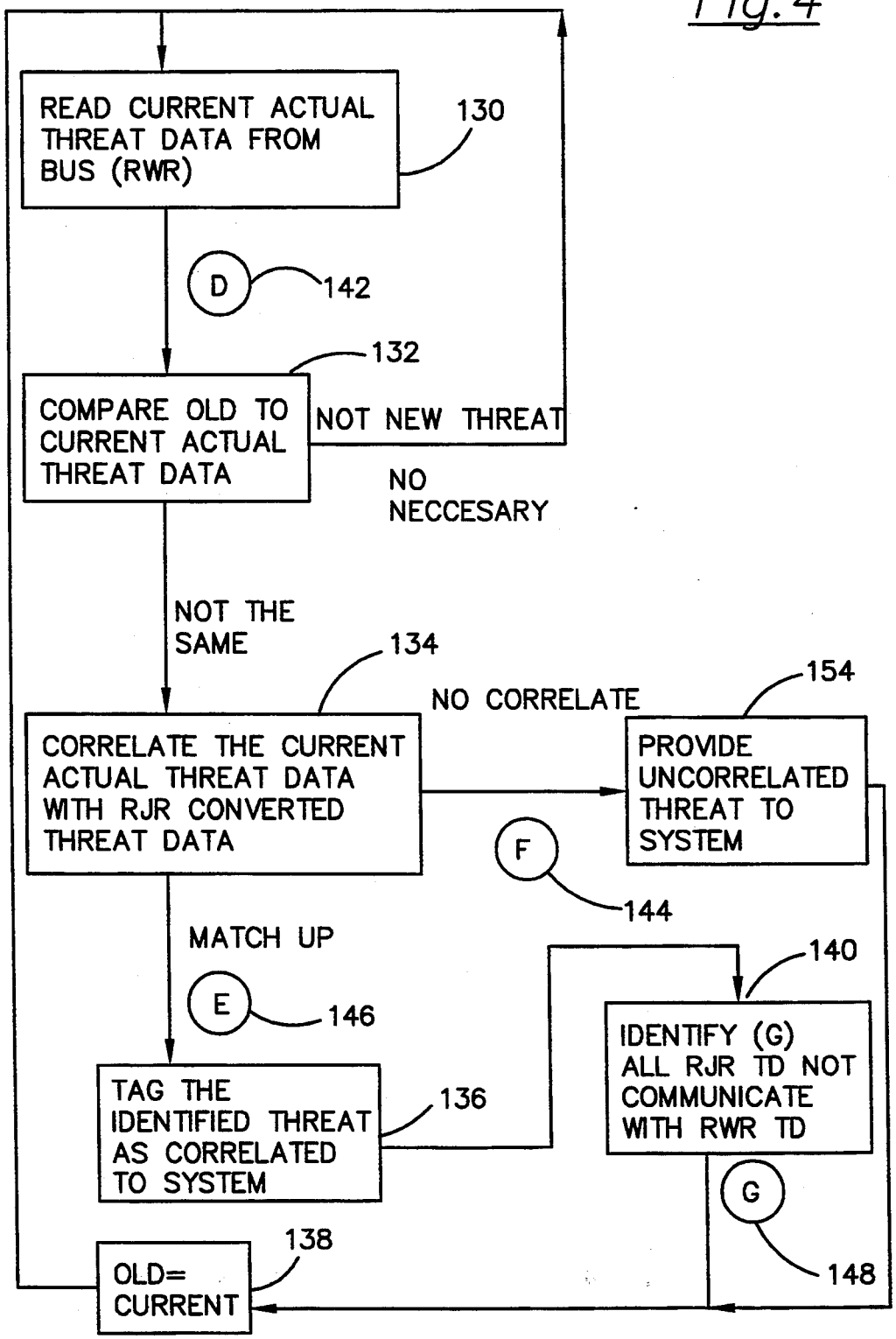
FIG. 4 shows one method of the invention used to perform data correlation on radar warning receiver data.

Referring now to FIG. 4, the method of the invention used to perform data correlation on radar warning receiver data is shown. The process starts at step 130 where the current actual threat data from the radar warning receiver is read from the data bus. The process 130 generates data set D 142. Data set D is then used by process step 132 to compare the current actual threat data with old threat data from the radar warning receiver. If the two threats are identical (i.e. the old and the current in step 132), the process returns to step 130 to read another actual threat. Step 130 reads in all available threats from the radar warning receiver. The set of all possible threats is commonly known as a threat set. In step 132, the old threat set is compared against a current actual threat set data. If the current actual threat set data is not a new threat set, then the process flows to 130 to scan another set of threats. In step 132, if there is a new threat, the process flows to step 134 to correlate the current actual threat set with the radar jamming receiver conferred at threat data which is generated in FIG. 3. The threat data is indicated by set B. If the converted threat data set. B correlates with the current actual threat data set, then the process flows to 136 to tag the identified threat set as a correlated new threat to the system using the method of the invention. The process then flows to step 140 where the process identifies a set G 148 which is all radar jamming receiver threat data that is not common with the radar warning receiver threat data. The process then flows to step 138 to set the old threat data set as the current threat data set for the next comparison and the next time cycle. The process then flows to 130 to read the next current actual threat data set from the bus.

If in step 134 there is no correlation between the current actual threat data set with the radar jamming receiver converted threat data set, the process flows to step 154, generates an un-correlated threat set F 144, and provides the un-correlated threat set to the system using the method of the invention.

As is the case with the jammer data, when implementing the method of the invention to convert the current actual threat data set from the radar warning receiver to either a correlated or un-correlated threat, the process creates various other data sets. Data set D 142 is the current active threat data set from the bus. Data set E 146 is the correlated current actual threat data with the radar jamming receiver converted threat data. Data set F 144 is the uncorrelated data. Data set G 148 is the data which is not common with the radar warning receiver threat data 148.

Now referring to FIG. 5, a data flow diagram showing the various data sets of the invention in a Venn diagram fashion is shown. Data set A 114 is the current actual jammer threat data. Data set B 118 is the correlated current actual jammer threat data or the converted set data. Data set C 116 is the un-correlated actual jammer threat data. Data set D 142 is current actual radar warning receiver threat data. Data set E 146 is the common current threat data. Data set F 144 is the un-correlated radar warning receiver threat data. Data set G 148 is the radar jamming receiver threat data which is not common with the radar warning receiver threat data. Data set G is used subsequently to generate a complementary threat set H 152. Data set H 152 is the complementary threat data set which represents the summation of data sets C and G.

The two basic processes shown in FIG. 3 and FIG. 4 are joined in this data flow diagram of FIG. 5. Two basic data sets include the data from the radar jamming receivers which is data set A 114, and the radar warning receiver which is data set D 142. The process of FIG. 3 generates the data set B 118 which represents all correlated current actual jammer threat data sets. This is used by both processes shown in FIG. 3 and FIG. 4 to create a complementary threat. The data set B 118 is subtracted from data set A 114 to generate data set C 116 which is the un-correlated current actual jammer threat data. Data set B 118 is also used along with the data set D 142 (current actual radar warning receiver threat data) to generate the intersection of the two data sets E 146. The data set E 146 is the common current threat data. The common current threat data is then subtracted from data set B 118 to generate a new data set G 148. Data set G 148 represents the radar jamming receiver threat data that is not common with the radar warning receiver threat data. That is, data set G 148 represents data from threats which are detected by the jammers, but not the radar warning receiver. Data set G 148 and data set C 116 are combined to create data set H which is called the complementary threat data. The complementary threat data set H comprises threats that are complementary to the already identified threats which have been identified by the radar warning receiver.

The system generates voice messages for radar warning and threat symbols and display windows for back-up threat representation.

Figure 6A:
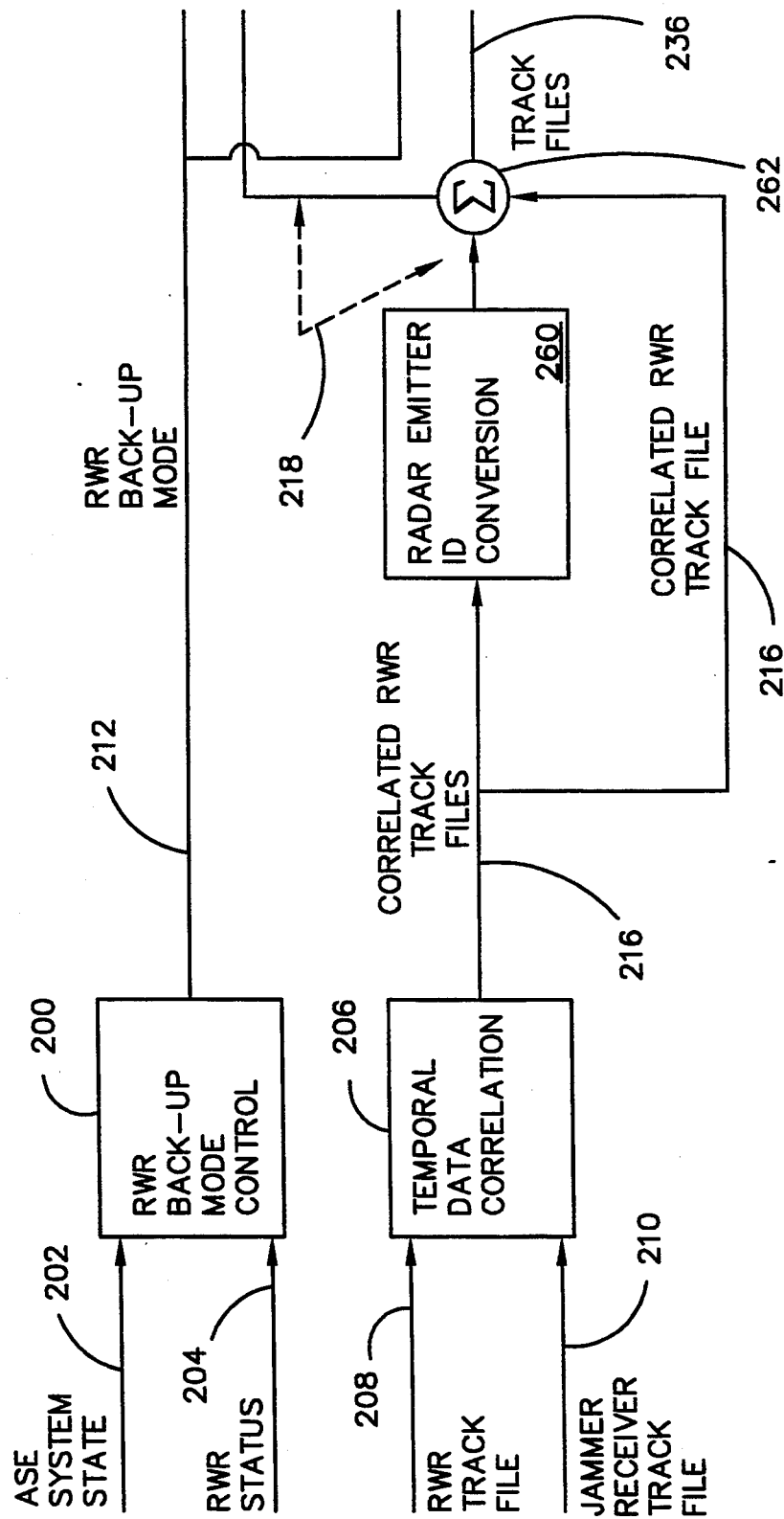
FIGS. 6A and 6B show a schematic block diagram for the functional radar warning receiver back-up generator.
Figure 6B:
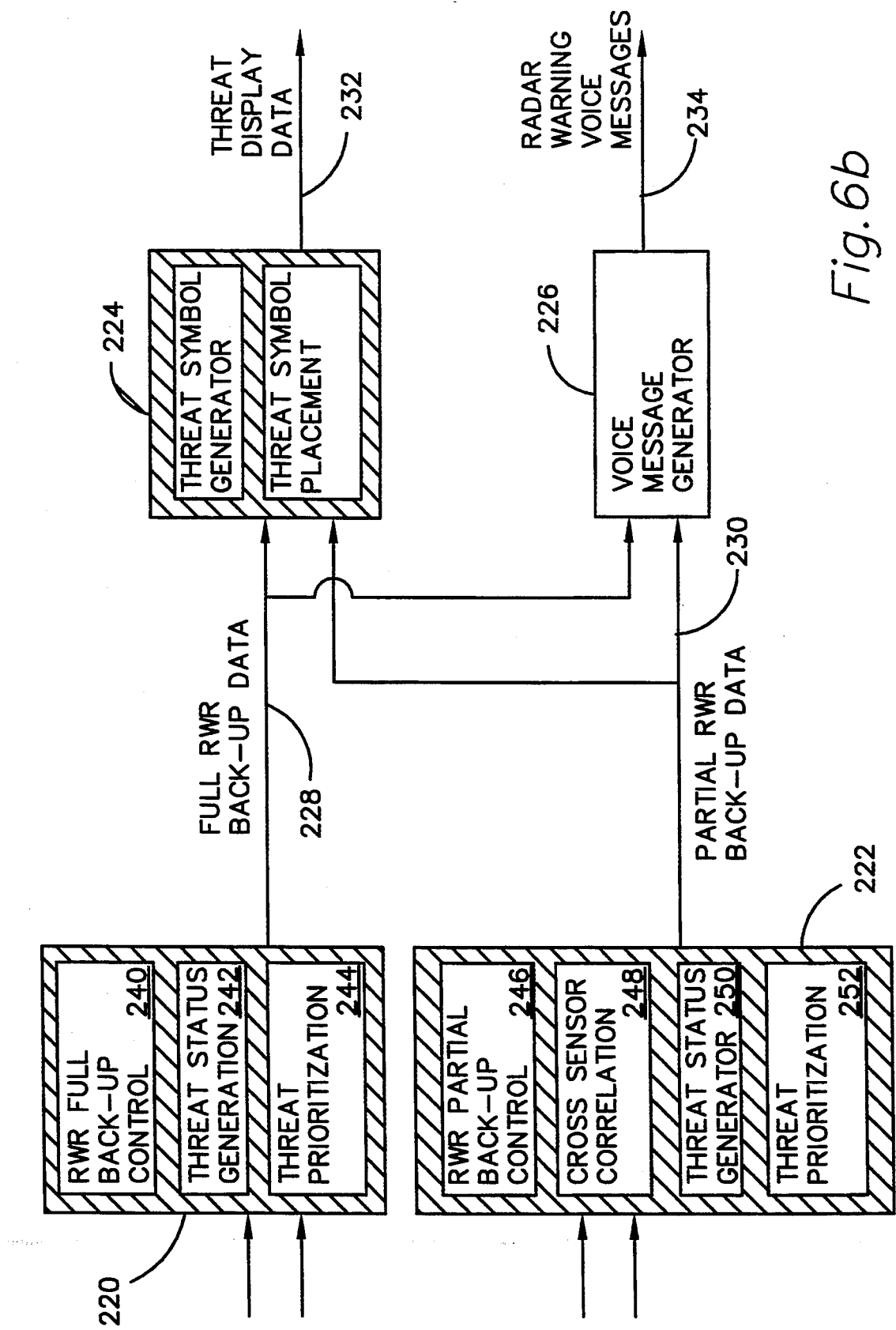

Now referring to FIG. 6 which shows a functional radar warning receiver back-up generator schematic block diagram. The ASE system state 202 is provided as an input to the radar warning receiver back-up mode control apparatus 200. The radar warning receiver status signal 204 is also provided as an input to the radar warning receiver back-up mode control apparatus 200. The radar warning receiver back-up mode control apparatus 200 has as an output the radar warning receiver back-up mode signal 212. This signal is provided to the functional radar warning receiver generator full back-up apparatus 220.

The full back-up apparatus 220 has three subfunctions. The first subfunction is a radar warning receiver full back-up control apparatus function 240. The second subfunction is the threat status generator function 242. The third subfunction is the threat prioritization function 244. The full back-up apparatus 220 has a full radar warning receiver back-up data signal 228 as an output. The full back-up apparatus 220 also has an input a converted track file 218.

The converted track file 218 is provided by the radar emitter conversion apparatus 260. The converted track file is also summed through summation junction 262 which sums a correlated radar warning receiver track file 216 with the output of the radar emitter ID conversion apparatus 260. The radar emitter ID conversion apparatus 260 has as an input, correlated radar warning receiver track file 216. The correlated radar warning receiver track file 216 is provided by the temporal data correlation apparatus 206. Temporal data correlation is provided between the radar warning receiver track file 208 and the jammer receiver track file 210.

The partial back-up apparatus 222 is provided with the radar warning receiver back-up mode signal 212 and the summed output signal track files 236 which is the sum of the output of the radar emitter ID conversion apparatus 260 and the correlated radar warning receiver track file 216. The partial radar warning receiver back-up apparatus 222 is composed of four subfunctions. The first subfunction is the radar warning receiver partial back-up control function 246. The second subfunction is the cross sensor correlation function 248. The third subfunction is the threat status generator function 250, and the fourth subfunction is the threat prioritization algorithm 252.

The partial back-up apparatus 222 provides a partial radar warning receiver back-up data signal 230 which is provided to two output apparatus. The first apparatus is the voice message generator 226 which produces radar warning voice messages 234. The second apparatus is the back-up display apparatus 224 which provides threat symbol generation along with threat symbol placement. The output of the display apparatus 224 is a threat display data signal 232.

The invention provides a functional RWR back-up capability based on functional redundancy. Radar warning receiver information such as radar detection data and radar identification data exists between the Radar Warning Receiver, the Pulsed Radar Jammer receiver, and CW Radar Jammer. The present invention provides an automatic back-up for both the voice and video functions of the Radar Warning Receiver. When an automatic backup is provided the system loses some of the threat coverage capability as indicated by the RWR system status or if the RWR system becomes inoperative.

The Functional RWR Back-up Generator apparatus of the invention is operated in two different modes: Partial RWR Back-up mode and, Full RWR Back-up mode. If the RWR system indicates that one or more isolated receivers have failed on RWR status line 204, then a RWR back-up function generating the partial RWR Back-up data is activated by partial back-up apparatus 222. Otherwise, if the RWR is either inoperative or not installed, then the function generating the full RWR back-up data is activated. Track files generated by the Radar Warning Receiver, Pulsed Radar Jammer, and CW Radar Jammer are processed by a Temporal Data Correlation apparatus 206 and a Radar Emitter ID Conversion apparatus 260 before being passed on to specific back-up functions.

Referring now to Table A which shows a correspondence between the quadrant of the radar warning receiver which has failed in the first column and the set of data used to provide the back-up data from the jammer hemispheres A and B and the surviving radar warning receiver quadrants 1, 2, 3 and 4.

TABLE A

| Correspondence | Failed Quadrant | Set Operations |
|---|---|---|
| 1 | 1 | B-4 |
| 2 | 2 | A-3 |
| 3 | 3 | A-2 |
| 4 | 4 | B-1 |
| 5 | 2 1 | A-3 and B-4 |
| 6 | 3 1 | A-2 and B-4 |
| 7 | 4 1 | B |
| 8 | 3 2 | A |
| 9 | 4 2 | A-3 and B-1 |
| 10 | 4 3 | A-2 and B-1 |
| 11 | 3 2 1 | A and B-4 |
| 12 | 4 2 1 | A-3 and B |
| 13 | 4 3 1 | A-2 and B |
| 14 | 4 3 2 1 | A and B |

The first correspondence backs up failed quadrant 1 of the radar warning receiver by providing set B from the radar jammer less set 4 from the radar warning receiver. Likewise, correspondence 2 provides back-up data for the failed quadrant of the radar warning receiver by subtracting the radar warning receiver set 3 from the jammer set A. Correspondence 5, for instance, provides back-up for failed quadrants 2 and from the radar warning receiver by "anding" the first subset, set A of the radar jammer less the third quadrant of the radar warning receiver, and the second subset, set B less the fourth quadrant of the radar warning receiver. Likewise, correspondence 14 provides back-up data for a failure of all quadrants of the radar warning receiver by anding the jammer sets A and B.

Figure 7:
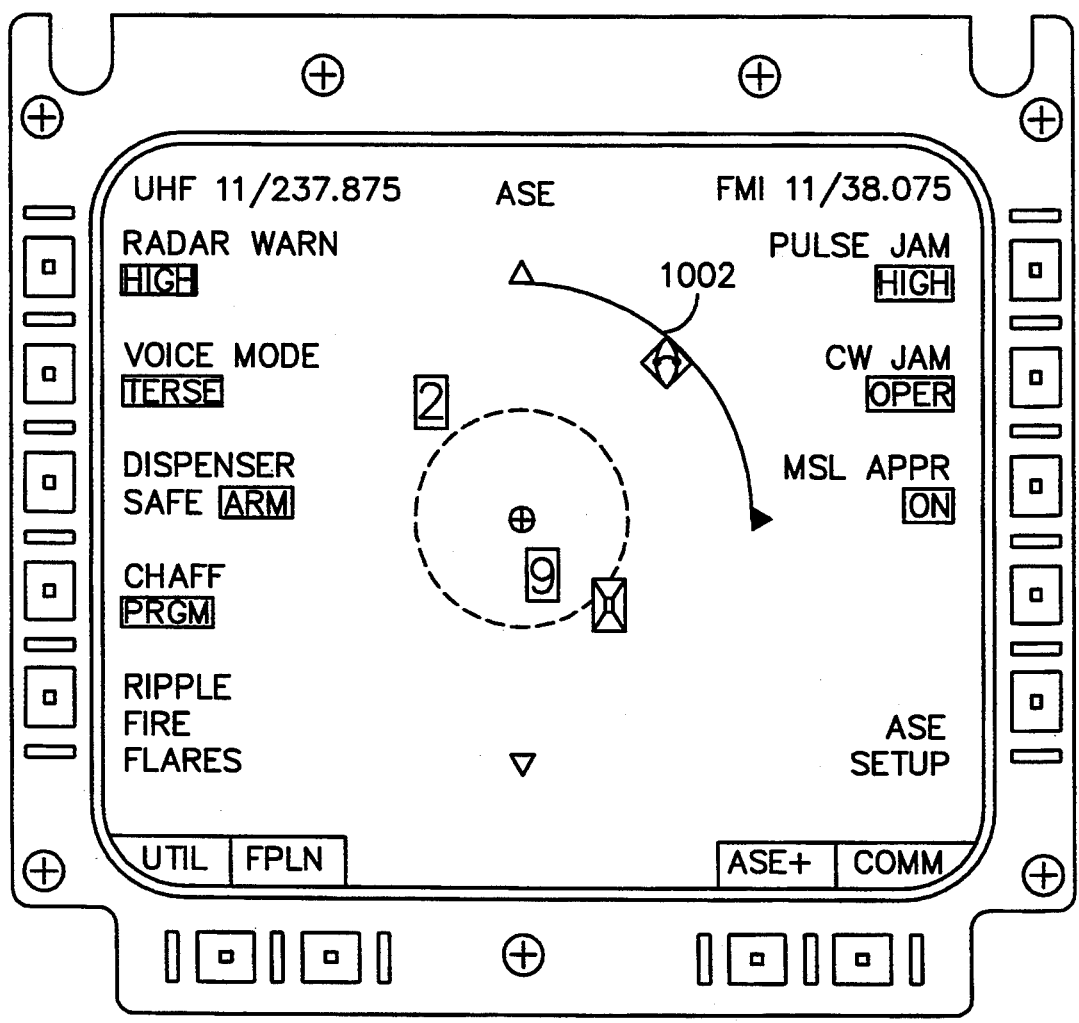
FIG. 7 shows a display diagram for the partial radar warning back-up first quadrant.

Now referring to FIG. 7 which shows a graphic display of the aircraft survivability display indicating partial radar warning receiver back-up in the first quadrant.

The partial RWR back-up apparatus and method of the invention determines which quadrant requires back-up threat generation. Quadrants are identified based on RWR system status. The failed quadrant is displayed with a solid arc segment 1002. The converted threat data is cross-sensor correlated to first, remove the common threats and second, provide the jamming status for RWR threats. The remaining threat data (un-correlated) is processed to determine threat display status such as "new", "old", and "aging-out". The method of the invention then provides a prioritization for these back-up threats. The threat data generated by the Partial RWR Back-up function is further processed by the video back-up display apparatus 224 to generate display threat data and by the voice apparatus 226 to generate radar warning voice messages. The video apparatus 224 and the voice apparatus 226 provide output to the aircraft crew.

The video apparatus 224 generates threat symbols based on threat type and operational mode for each back-up threat and provides proper space separation between threats. The back-up threats are placed inside a window located on the periphery of the threat circle.

The voice apparatus 226 generates radar warning voice messages based on the provided back-up threat data. The function uses the information included in the back-up data such as threat type, threat status, threat mode, etc. to properly generate brief and concise voice messages.

Figure 8:
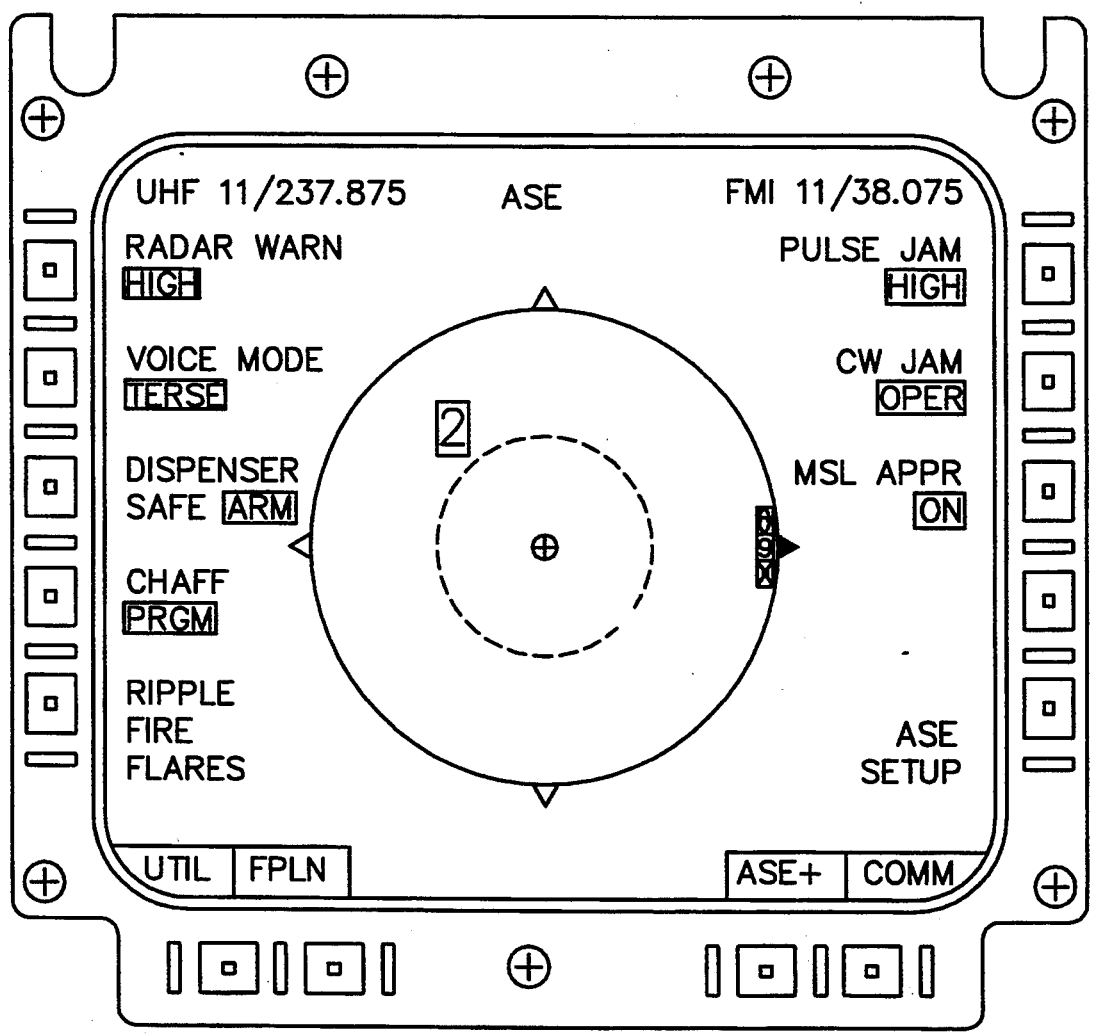
FIG. 8 shows a display diagram for the radar warning receiver of full back-up threat display.

Now referring to FIG. 8 which shows a display diagram for the radar warning receiver full back-up threat display.

The full RWR back-up function of the invention provides a full RWR back-up. It processes the converted threat data from the Pulsed Radar Jammer and CW Radar Jammer to determine the threat display status. This is a data processing technique similar to what is used in the Partial RWR Back-up function. Threats contained in the back-up list are prioritized before being passed on to the Video function and the Voice function. Thee display format for the full RWR back-up is shown in FIG. 8.

In the event the Radar Warning Receiver loses some or all of its threat detection capability, this process automatically provides either partial or full functional back-up of the RWR according to Table A. Since there are two levels of RWR failure, partial or total, there are two back-up sub-processes providing two different back-up modes, the Partial RWR Back-up mode and Full RWR Backup mode.

The Partial RWR Back-up mode monitors the RWR status to determine when a failure has occurred in one or more channels of the receiver quadrants. When a failure is detected, the process begins to process PRJ data to augment the RWR threat warning function in the region where RWR coverage has failed.

In one embodiment of the invention a video back-up is provided and voice warnings are not generated to avoid overlaps with RWR generated voice warnings.

The Perform Full RWR Back-up function 240 monitors the RWR for a complete RWR system failure. In the event a system failure occurs, threat detection data from the radar jammers is processed to provide warning data to the crew. Full voice warning back-up is provided by the ASE/ACS in this mode. Neither of these back-up functions are invoked if the radar jammer subsystems are not installed on the aircraft.

The invention can be realized in alternate embodiments, one identifying only common threats which can be detected and identified by the Radar Warning Receiver. An alternate embodiment provides voice and/or video for the back-up threats. Yet another embodiment employs a prioritization scheme where threat symbols and voice messages of the Radar Warning Receiver are generated.

The perform partial RWR backup function 246 operates during a partial failure of the RWR. This failure condition is indicated by the system status of the Radar Warning Receiver status line 204. When this condition occurs, the Perform Partial RWR Back-up process is initiated. This process uses threat detection data from the installed and operating jammer subsystems to generate Warning information in the failed RWR quadrant(s). The radar jammer track files 210 are only processed for common threats in this mode. Those skilled in the art will recognize that un-correlated threats do not exist in the failed quadrant. By definition jammer unique threats continue to be displayed as complementary threats. The RWR prioritization display rules are used to display the back-up data.

The method of the invention continuously monitors the ASE system state 202 to determine when to provide the RWR partial backup. In one embodiment of the invention, the ASE system state is set equal to 9 to 15 inclusively. In the event the jammers are not installed or both have failed, this sub-process is invoked. Given that one or both of the jammers are available to support the, back-up function, this process monitors the bit settings in the System Status output message from the Radar Warning Receiver to determine if a failure has occurred and the extent of the failure. If a partial failure is indicated, the Partial Back-up mode is invoked; if a total RWR failure is indicated, the Full Back-up mode is invoked. In the case of Partial Back-up, there are six basic data subprocesses that are required to support different partial failure modes of the RWR. The subprocesses are described below.

Subprocess 1

If the right channel of the forward receiver fails (i.e. bit 1, word 2 of the bus message is set equal to one (1)), RF threats located in the first quadrant are not detected by the RWR. This back-up sub-process uses radar emitter track file data for threats received by the CW Radar Jammer and from tile right antenna of the Pulsed Radar Jammer. The Pulsed Radar Jammer data must be further processed to extract threats already detected by the RWR in the still functioning second quadrant. The steps invoked in this sub-process are outlined herein:

Step 1

The jammer emitter identifications (ID) contained in the radar jammer track files are converted to compatible radar warning emitter ID's. Only common convertible emitters are used for back-up while the remaining unique emitters are presented as complementary threats.

Step 2

Threats from the RWR track file having an AOA between 270 and 360 degrees is extracted from and compared to the appropriate portions of the radar jammer active threat track file (i.e. the CW detection file and that from the right antenna of the Pulsed Radar Jammer). If a match occurs, that threat emitter is marked as "common" and removed from the radar jammer active threat track file.

Step 3

Emitters remaining in the track file from Step 2 are prioritized for display. These threat symbols are displayed along a 45 degree radial on the RWR display area. Additionally, a ninety degree solid arc segment 1002 is displayed from 0 to 90 degrees on the perimeter of the RWR display to indicate that the Radar Warning Receiver has failed in that region and that radar jammer data with degraded angular resolution is being used to provide RF warning therein.

Sub Process 2

If the left channel of the forward receiver fails (i.e. bit 00, word 2 of the data bus message is set equal to a one (1)), RF threats located in the fourth quadrant are not detected by the RWR. This back-up sub-process uses radar emitter track file data for threats received by the CW Radar Jammer and from the left antenna of the Pulsed Radar Jammer. The Pulsed Radar Jammer data must be further processed to extract threats already detected by the RWR in the still functioning third quadrant. The steps involved in this sub-process are outlined below:

Step 1

The jammer emitter identifications (ID) contained in the radar jammer track files are converted to compatible radar warning emitter ID's. Only common convertible emitters are used for back-up while the remaining unique emitters are presented as complementary threats.

Step 2

Threats from the RWR track file having an AOA between 180 and 270 degrees are extracted from and compared to the appropriate portions of the radar jammer active threat track file (i.e. the CW detection file and that from the right antenna of the Pulsed Radar Jammer). If a match occurs, that threat emitter is marked as "common" and removed from the radar jammer active threat track file.

Step 3

Emitters remaining in the track file from Step 2 are prioritized for display based on predefined prioritization rules. These threat symbols are displayed along a 135 degree radial on the RWR display area. Additionally, a ninety degree solid arc segment is displayed from 90 to 180 degrees on the perimeter of the RWR display to indicate that the Radar Warning Receiver has failed in that region and that radar jammer data with degraded angular resolution is being used to provide RF warning therein.

Subprocess 3

If the left channel of the aft receiver fails (i.e. bit 02, word 02 of the data bus message is set equal to a one (1)), RF threats located in the third quadrant are not detected by the RWR. This back-up sub-process uses radar emitter track file data for threats received by the CW Radar Jammer and from the left antenna of the Pulsed Radar Jammer. The Pulsed Radar Jammer data must be further processed to extract threats already detected by the RWR in the still functioning fourth quadrant. The steps involved in this subprocess are outlined below:

Step 1

The jammer emitter identifications (ID) contained in the radar jammer track files are converted to compatible radar warning emitter ID's. Only common convertible emitters are used for back-up while the remaining unique emitters are presented as complementary threats.

Step 2

Threats from the RWR track file having an AOA between 90 and 180 degrees are extracted from and compared to the appropriate portions of the radar jammer active threat track file (i.e. the CW detection file and that from the right antenna of the Pulsed Radar Jammer). If a match occurs, that threat emitter is marked as "common" and removed from the radar jammer active threat track file.

Step 3

Emitters remaining in the track file from Step 2 are prioritized for display based on predefined prioritization rules. These threat symbols are displayed along a 225 degree radial on the RWR display area. Additionally, a ninety degree solid arc segment is displayed from 180 to 270 degrees on the perimeter of the RWR display to indicate that the Radar Warning Receiver has failed in that region and that radar jammer data with degraded angular resolution is being used to provide RF warning therein.

Subprocess 4

If the right channel of the aft receiver fails (i.e. bit 03, word 02 of the data bus message is set equal to a one (1)) and RF threats located in the second quadrant are not detected by the RWR. This back-up sub-process uses radar emitter track file data for threats received by the CW Radar Jammer and from the right antenna of the Pulsed Radar Jammer. The Pulsed Radar Jammer data must be further processed to extract threats already detected by the RWR in the still functioning first quadrant. The steps involved in this subprocess are outlined herein:

Step 1

The jammer emitter identifications (ID) contained in the radar jammer track files are converted to compatible radar warning emitter ID's. Only common convertible emitters are used for back-up while the remaining unique emitters are presented as complementary threats.

Step 2

Threats from the RWR track file having an AOA between 0 and 90 degrees are extracted from and compared to the appropriate portions of the radar jammer active file (i.e. the CW detection file and that from the right antenna of the Pulsed Radar Jammer). If a match occurs, that threat emitter is marked as "common" and removed from the radar jammer active threat track file.

Step 3

Emitters remaining in the track file from Step 2 are prioritized for display based on predefined prioritization rules. These threat symbols are displayed along a 315 degree radial on the RWR display area. Additionally, a ninety degree solid arc segment is displayed from 270 to 360 degrees on the perimeter of the RWR display to indicate that the Radar Warning Receiver has failed in that region and that radar jammer data with degraded angular resolution is being used to provide RF warning therein.

Subprocess 5

If both left channels of the forward and aft receivers fail (i.e. bit 00 and bit 02, word 02 of the data bus message are set equal to one (1)), RF threats located on the third and fourth quadrants will not be detected by the RWR. This backup sub-process uses radar emitter track file data for threats received by the CW Radar Jammer and from the left antenna of the Pulsed Radar Jammer. Similarly, Steps 1 and 3 are used in this sub-process, but not Step 2. These threat symbols are displayed along a 180 degree radial on the RWR display area. Additionally, a one hundred-eighty degree solid arc segment is displayed from 90 to 270 degrees on the left side of the perimeter of the RWR display to indicate that the Radar Warning Receiver has failed in that region, and that radar jammer data with a degraded angular resolution is being used to provide an RF warning therein.

Subprocess 6

If both right channels of the forward and aft receivers fail (i.e. bit 01 and bit 03 of data word 02 of the data bus message are set equal to one (1)), RF threat located on the first and second quadrants will not be detected by the RWR. This back-up sub-process uses radar emitter track file data for threats received by the CW Radar Jammer and from the right antenna of the Pulsed Radar Jammer. Similarly, Steps 1 and 3 are used in this sub-process, but not Step 2. These threat symbols are displayed along a 0 degree radial on the RWR display area. Additionally, a one hundred-eighty degree solid arc segment is displayed from 90 to 270 degrees on the right side of the perimeter of the RWR display to indicate that the Radar Warning Receiver has failed in that region, and that radar jammer data with degraded angular resolution is being used to provide an RF warning.

As multiple quadrant failures occur within the RWR, the appropriate combination of the above sub-processes are employed as necessary. If all four quadrants fail, the ASE/ACS invokes the Full Back-up mode.

Back-up threats are displayed as described in the above sub-processes. Their display placement is defined by the RWR prioritization tables. The highest priority threat appears on the top and is then followed by lower priority threats.

In one preferred embodiment of the invention this process is performed at the rate of 2 Hz (±0.1 Hz) or faster.

In the event the Radar Warning Receiver is not installed or has completely failed, the aircraft survivability method and apparatus of the invention invokes the Full Back-up process. This process uses RF receive data from the active radar jammer systems and displays this information as complementary threats due to the lack of the angle of the arrival data. Threats are displayed based upon the RWR prioritization criteria.. Voice messages are also generated by the system. This process is not invoked if the jammers are not installed or are not functional.

The Full Back-up process is invoked if the ASE system state indicates that the Radar Warning Receiver is either inoperative or is not installed and either or both the Pulsed Radar Jammer and CW Radar Jammer are functional (i.e. ASE system state 202 is set equal to 17, 18, or 21 for the PRJ or is set equal to 17, 18, or 20 for the CWJ). Jammer track files are processed to convert the RWR compatible threats to the RWR threat emitter ID's for the purpose of generating voice warning messages. Un-correlated threats continue to be processed as complementary threats.

The process of generating back-up RWR display symbols and voice warnings requires the execution of the following functions: threat emitter ID conversion, threat prioritization, voice message generation, and threat display.

The pulse radar emitter ID's generated by the Pulsed Radar Jammer are processed for conversion to RWR-compatible emitter ID's. The radar emitter ID generated by the CW Radar Jammer is processed for conversion to a RWR-compatible emitter ID. Corrected threats are passed on for prioritization and voice warning generation. Un-correlated threats are processed as complementary threats.

Convertible RF threat emitters are prioritized based on a predefined prioritization scheme.

The ASE/ACS prioritizes and generates voice warning messages based upon the threat emitter ID list passed from the threat emitter ID conversion sub-process. These messages are generated using predetermined RWR Voice Warning Generation rules.

Threat symbols for the threat emitter ID list passed from the threat emitter ID conversion sub-process are generated based on predetermined RWR display rules.

Without the AOA RWR data, it is necessary to display all threats as complementary. The threat detected by the CW Radar Jammer is displayed in the window at the top of the RWR display area. Threats detected by the Pulse RF Jammer are displayed in the left or right hand complementary threat window depending on which side of the aircraft the threat was detected on.

A predetermined the:eat placement rule is used to place the back-up threats in the defined windows. The threat with a higher priority is displayed first and followed by the lower priority threats. This process is performed at the rate of 2 Hz (±0.1 Hz) or faster.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A functional radar warning receiver back-up apparatus comprising:
  (a) pulsed radar jammer means having a first radar identification data output;
  (b) continuous wave radar jammer means having a second radar identification data output;
  (c) temporal correlation means operatively connected to said first and second radar identification data outputs for providing temporal data correlation between said first radar identification data output and said second radar identification data output to therefrom provide functional radar warning information to a radar warning information output; and
  (d) radar emitter ID conversion means operative connected to temporal correlation means for providing converted information.

2. The functional radar warning receiver back-up apparatus of claim 1 wherein said functional radar warning information provided by said temporal correlation means further includes radar warning receiver information received from a radar warning receiver pulsed radar jammer information and continuous wave radar jammer information, the functional radar warning receiver back-up apparatus further comprising cross data correlation means for identifying any data common to said radar warning receiver information said pulsed radar jammer information and said continuous wave radar jammer information.

3. The functional radar warning receiver back-up apparatus of claim 1 further comprising voice generator means for warning a pilot of a threat.

4. The functional radar warning receiver apparatus of claim 1 further comprising video display means for communicating detected threats to a pilot.

5. A functional radar warning receiver back-up generator apparatus comprising:
  (a) radar back-up mode control means for providing a radar warning receiver back-up mode signal, said control means having an aircraft survivability system state input and a radar warning receiver status input;

(b) full radar warning receiver back-up generator apparatus for providing full radar warning receiver back-up data, said generator apparatus having an input connected to receive the radar warning receiver back-up mode signal and a converted track file input;

(c) temporal data correlation means for providing a correlated track file output having a radar warning receiver track file input and a jammer receiver track file input;

(d) radar emitter ID conversion means operatively connected to the correlated track file output for providing a converted track file output; and (e) means for summing the converted track file output and the correlated radar warning receiver radar warning receiver track file output to produce a summed output signal track file.

6. The functional radar warning receiver back-up generator apparatus of claim 5 further comprising a partial radar warning receiver back-up means operatively connected to receive the summed output signal track file and the radar warning receiver back-up mode signal.

7. The functional radar warning receiver back-up generator of claim 5 further comprising voice message generator means for announcing the full radar warning receiver back-up data.

8. The functional radar warning receiver back-up generator of claim 7 further comprising voice message generator means for announcing partial radar warning back-up data.

9. The functional radar warning receiver back-up generator of claim 5 comprising means for presenting the full radar warning back-up data on an aircraft survivability equipment display using threat symbol placement means and a threat symbol generator.

10. The functional radar warning receiver back-up generator of claim 6 comprising means for presenting the partial radar warning back-up data on an aircraft survivability equipment display using threat symbol placement means and a threat symbol generator.

11. A method for using a functional radar warning receiver back-up generator backed up by a radar jammer wherein the radar jammer has a first A hemisphere and second B hemisphere and the radar warning receiver has first, second, third, and fourth quadrants, the jammer providing a set A of threats and a set B of threats corresponding to hemispheres A and B, respectively, and the radar warning receiver providing a set 1 of threats corresponding to the first quadrant, a set 2 of threats corresponding to the second quadrant, a set 3 of threats corresponding to the third quadrant and a set 4 of threats corresponding to the fourth quadrant wherein the method comprises the steps of:

(a) providing set B minus set 4 to back-up failed quadrant 1;

(b) providing set A minus set 3 to back-up failed quadrant 2;

(c) providing set A minus set 2 to back-up failed quadrant 3;

(d) providing set B minus set 1 to back-up failed quadrant 4;

(e) providing set A minus 3 and set B minus 4 for backing up failed quadrants 2 and 1;

(f) providing set A minus set 2 and set B minus set 4 to back-up quadrants 3 and 1;

(g) providing set B to back-up quadrants 4 and 1;

(h) providing set A to back-up failed quadrants 3 and 2;

(i) providing set A minus set 3 and B minus set 1 to back-up failed quadrants 4 and 2;

(j) providing set A minus set 2 and set B minus set 1 to back-up failed quadrants 4 and 3;

(k) providing set A and set B minus set 4 to back-up failed quadrants 3, 2 and 1;

(l) providing set A minus set 3 and set B to back-up failed quadrants 4, 2 and 1;

(m) providing set A minus set 2 and set B to back-up failed quadrants 4, 3 and 1; and (n) providing set A and set B to back-up failed quadrants 4, 3, 2 and 1.

12. An integrated aircraft survivability equipment apparatus comprising:

(a) data bus means having a data bus control input;

(b) means for aircraft survivability integration having a multifunction display output, a data bus control output connected to the data bus control input, a radar warning receiver control output, a pulsed radar jammer control output, a continuous wave radar jammer control output, and a missile approach detector control output;

(c) radar warning receiver means connected to the data bus means and having a radar warning receiver control input connected to the radar warning receiver control output;

(d) pulsed radar jammer means connected to the data bus means having a pulsed radar jammer control input connected to the pulsed radar jammer control output;

(e) continuous wave radar jammer means connected to the data bus means having a continuous wave radar jammer control input connected to the continuous wave radar jammer control output;

(f) missile approach detector means connected to the data bus means having a missile approach detector control input connected to the missile approach detector control output;

(g) multifunction display means having a multifunction display input connected to the multifunction display output, the multifunction display means further connected to a keyboard control unit, the means for aircraft survivability integration further having functional radar warning receiver back-up means connected to the data bus means for backing-up the radar warning receiver means in the event of partial or complete failure of the radar warning receiver means.

13. The integrated aircraft survivability equipment apparatus of claim 12 wherein the functional radar warning receiver back-up apparatus comprises temporal correlation means for providing temporal data correlation between the radar warning receiver means output and the pulsed and continuous wave jammer means outputs.

14. The integrated aircraft survivability equipment apparatus of claim 13 wherein the functional radar warning receiver back-up apparatus further comprises partial back-up means for identifying any common data generated from the radar warning receiver means, the pulsed radar jammer means and the continuous wave radar jammer means.

15. The integrated aircraft survivability equipment apparatus of claim 13 further comprising radar emitter ID conversion means to provide.

16. The integrated aircraft survivability equipment apparatus of claim 13 further comprising voice generator means for warning the pilot of a threat.

17. The integrated aircraft survivability equipment apparatus of claim 13 further comprising video display means for communicating detected threats to a pilot.

* * * * *